US011891671B1

(12) United States Patent
Resquin

(10) Patent No.: US 11,891,671 B1
(45) Date of Patent: Feb. 6, 2024

(54) VIRUS DETECTION SYSTEM

(71) Applicant: A9.com, Inc., Palo Alto, CA (US)

(72) Inventor: Carlos Roberto Resquin, Buenos Aires (AR)

(73) Assignee: A9.com, Inc., Palo Alto, CA (US)

( * ) Notice: Subject to any disclaimer, the term of this patent is extended or adjusted under 35 U.S.C. 154(b) by 191 days.

(21) Appl. No.: 17/210,832

(22) Filed: Mar. 24, 2021

(51) Int. Cl.
*B01L 3/00* (2006.01)
*G01N 21/64* (2006.01)
*C12Q 1/70* (2006.01)

(52) U.S. Cl.
CPC .............. *C12Q 1/70* (2013.01); *B01L 3/5027* (2013.01); *B01L 3/502753* (2013.01); *G01N 21/645* (2013.01); *G01N 21/6428* (2013.01); *G01N 2021/6471* (2013.01)

(58) Field of Classification Search
None
See application file for complete search history.

(56) References Cited

U.S. PATENT DOCUMENTS

| | | | | |
|---|---|---|---|---|
| 5,961,451 | A * | 10/1999 | Reber | A61B 5/14532 250/341.1 |
| 9,040,288 | B2 * | 5/2015 | Handique | F16K 99/003 435/303.1 |
| 2003/0142291 | A1 * | 7/2003 | Padmanabhan | G01N 15/1484 356/39 |
| 2009/0253181 | A1 * | 10/2009 | Vangbo | B01L 3/502738 204/453 |
| 2011/0201099 | A1 * | 8/2011 | Anderson | G01N 1/10 422/68.1 |
| 2011/0312841 | A1 * | 12/2011 | Silverbrook | C12Q 1/68 506/40 |
| 2014/0194305 | A1 * | 7/2014 | Kayyem | C12Q 1/6825 506/18 |
| 2017/0241949 | A1 * | 8/2017 | Bort | B01L 3/502792 |

* cited by examiner

*Primary Examiner* — Neil N Turk
(74) *Attorney, Agent, or Firm* — Kilpatrick Townsend & Stockton LLP

(57) ABSTRACT

Systems for testing for a target virus include an analysis device and a sample cartridge. A system for detecting a target virus includes a cartridge and an analysis device. A biological sample is inserted into the cartridge. The cartridge includes reagents and other liquids for processing the biological sample. The cartridge is inserted into the analysis device. The analysis device interacts with the cartridge to complete testing of the biological sample for the presence of the target virus.

14 Claims, 13 Drawing Sheets

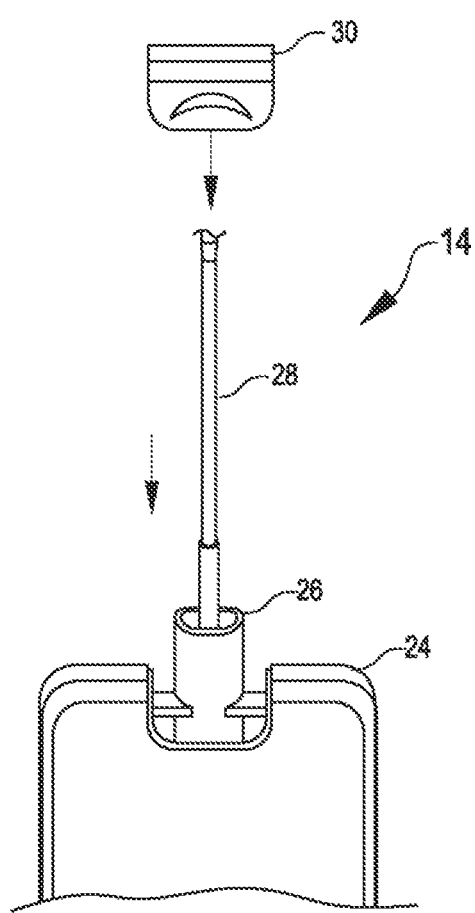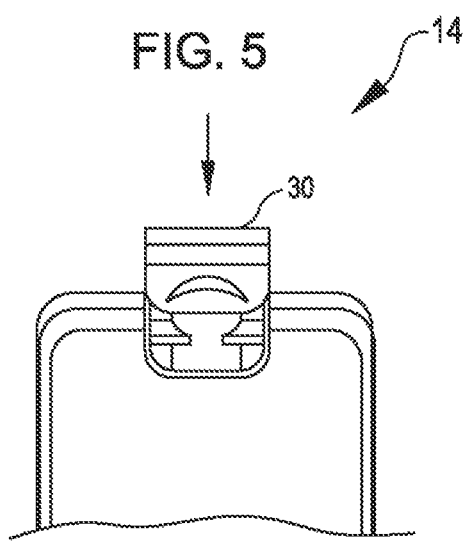

VIRUS DETECTION SYSTEM

BACKGROUND

Timely and accurate detection of a virus is important to enabling timely and effective treatment of a person infected with the virus. Timely and accurate detection of the virus can also help to inhibit spreading of the virus from the infected person via suitable precautions taken based on knowing that the person is infected with the virus. Timely and accurate detection of a virus is especially important where the virus has a high lethality in at least some vulnerable populations (e.g., elderly, diabetic, immune compromised), such as with the SARS-CoV-2 virus.

BRIEF DESCRIPTION OF THE DRAWINGS

Various embodiments in accordance with the present disclosure will be described with reference to the drawings, in which:

FIG. 4 shows a view of the cartridge of the system of FIG. 1 illustrating insertion of a swab into a swab tube of the cartridge, in accordance with embodiments;

FIG. 5 shows a view of the cartridge of the system of FIG. 1 illustrating capping of the swab tube following insertion of a swab into the cartridge, in accordance with embodiments;

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

A system and related method for detecting whether a biological sample includes a target virus is described. In many embodiments, an analysis device is used in conjunction with a single-use cartridge to test a biological sample for the presence of the target virus. The system can be adapted for detecting any suitable virus including, but not limited to, SARS-CoV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V. The system can be used at the point of care, including in very low complexity medical environments. The system can also be used in any other suitable location, such as in a house.

The analysis device and single-use cartridge can be used to test for the presence of the target virus in a biological sample taken with a swab, nasal or nasopharyngeal. In many embodiments, the analysis device delivers a result in real-time, transmitted to a mobile device application, through a suitable communication connection (e.g., USB cable, WiFi, Bluetooth, etc.).

The system is configured to amplify and detect a target virus (e.g., SARS-CoV-2 viral RNA) from a patient's nasal swab. The system includes a single-use cartridge and the analysis device into which the cartridge is inserted. In many embodiments, the system employs isothermal amplification of viral RNA via RT-LAMP and subsequent detection using CRISPR/Cas technology, eventually resulting in a detectable fluorescent signal from cleaved fluorescein (FAM) reporters.

Figure 1:
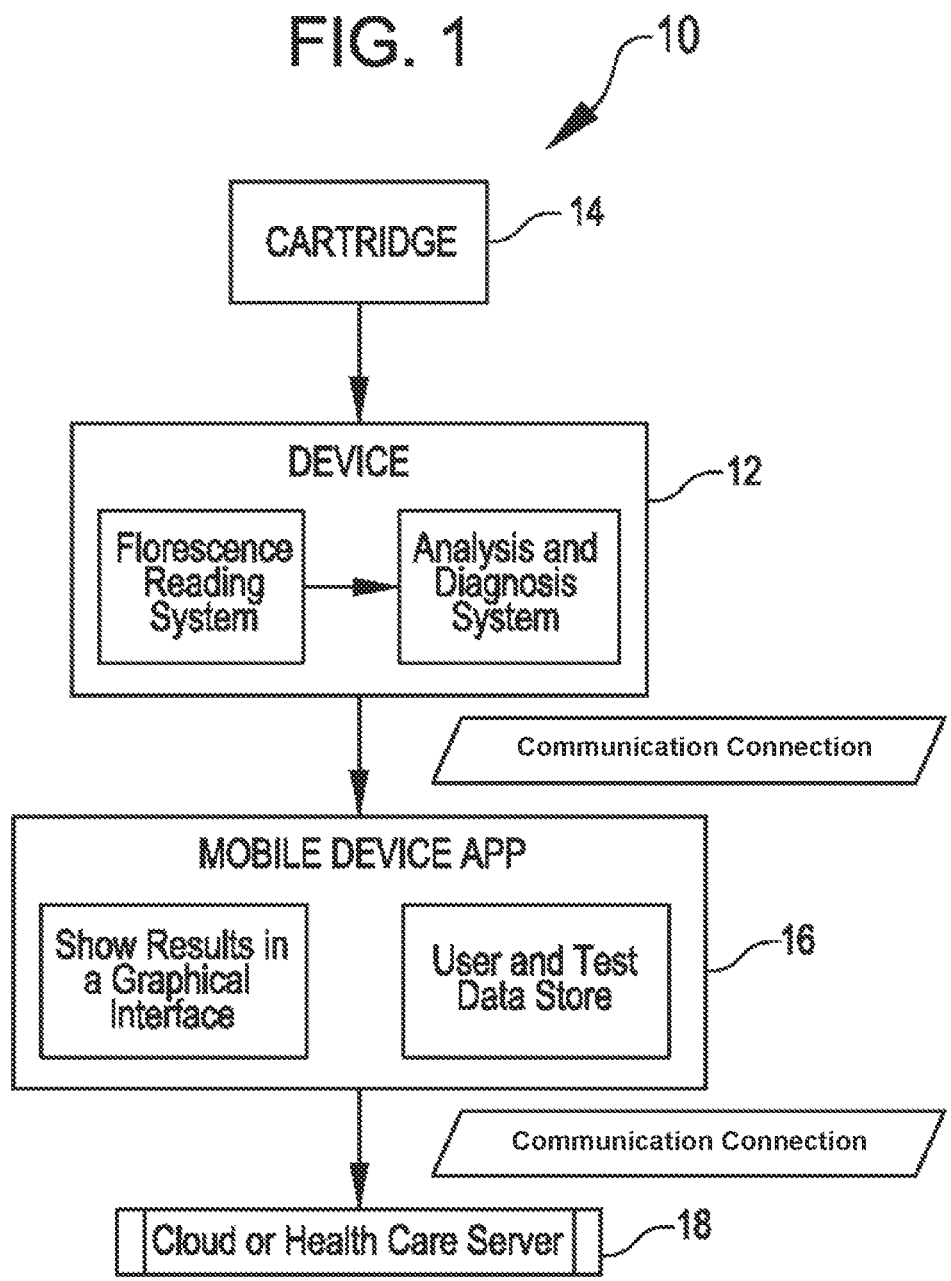
FIG. 1 is a simplified schematic diagram of a system for detecting whether a target virus is present in a biological sample, in accordance with embodiments.

Turning now to the drawing figures, in which similar reference identifiers refer to similar elements, FIG. 1 is a simplified schematic diagram of a system 10 for detecting whether a target virus is present in a biological sample, in accordance with embodiments. The system 10 includes an analysis device 12, a single use cartridge 14, and an electronic device 16. In many embodiments, a biological sample is taken with a swab, the swab is inserted into the cartridge 14, the cartridge 14 is inserted into the analysis device 12, the analysis device 12 interacts with the cartridge 14 to detect whether the target virus is present in the biological sample, and the analysis device 12 communicates with the electronic device 16 to either transmit a detection result to the electronic device 16 or transmit test data to the electronic device 16 by which the electronic device 16 can determine the detection result. The electronic device 16 can communicate with a health care server 16 to either transmit a detection result to the healthcare server 18 or transmit test data to the healthcare server 18 by which the healthcare server 18 can determine the detection result. While the system 10 is described herein with respect to detection of the SARS-CoV-2 virus, the system 10 can be adapted for use in detection of any suitable virus including, but not limited to, the viruses listed herein.

Figure 2:
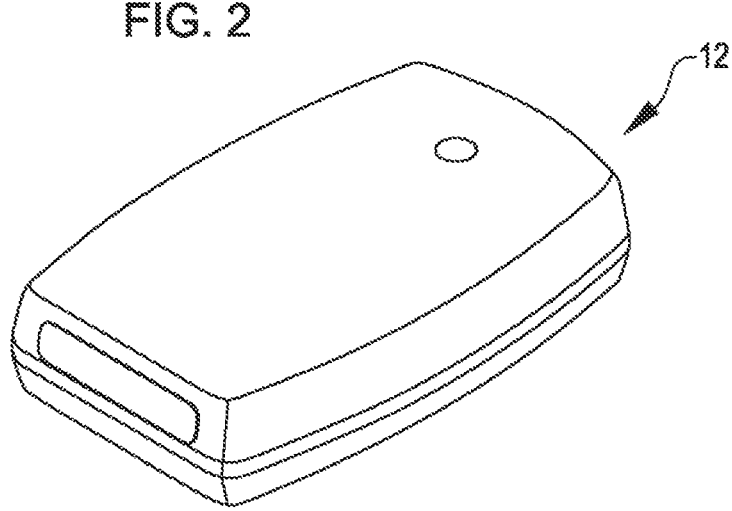
FIG. 2 shows the analysis device of the system of FIG. 1 in a closed configuration, in accordance with embodiments.
Figure 3:
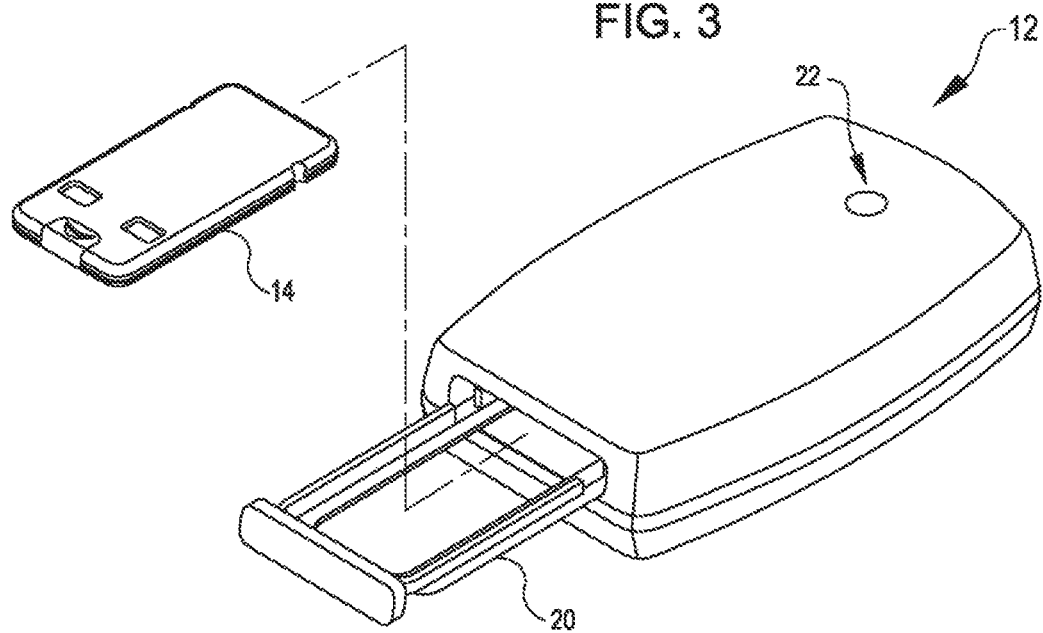
FIG. 3 shows the analysis device of the system of FIG. 1 in an open configuration and a cartridge for the analysis device, in accordance with embodiments.

FIG. 2 and FIG. 3 show the analysis device 12 and the cartridge 14. FIG. 3 shows the analysis device 12 in an open configuration for receiving the cartridge 14 by a cartridge support 20 for retraction into the analysis device 12. The analysis device 12 includes a start button 22 that can be pressed to reconfigure the analysis device 12 from the closed configuration shown in FIG. 2 to the open configuration shown in FIG. 3.

In many embodiments, the cartridge 14 includes an outer shell 24 and a swab tube 26. The swab tube 26 is configured to enclose a sample swab 28 containing a biological sample to be tested to determine whether the biological sample includes the target virus. FIG. 4 shows a view of the cartridge 14 illustrating insertion of a sample swab 28 into the swab tube 26. FIG. 5 shows a view of view of the cartridge 14 illustrating fitting of a swab tube cap 30 to the swab tube 26 to enclose the sample swab 28 within the cartridge 14. The sample swab to be used can be standard from any manufacturer as long as the length of the sample swab is not greater than a maximum length of sample swap that can be accommodated by the cartridge 14. For example, in some embodiments, the cartridge 14 is capable of accepting a sample swab with a length up to 80 mm, after separation of the sample swab handle from the sample swab.

Figure 6:
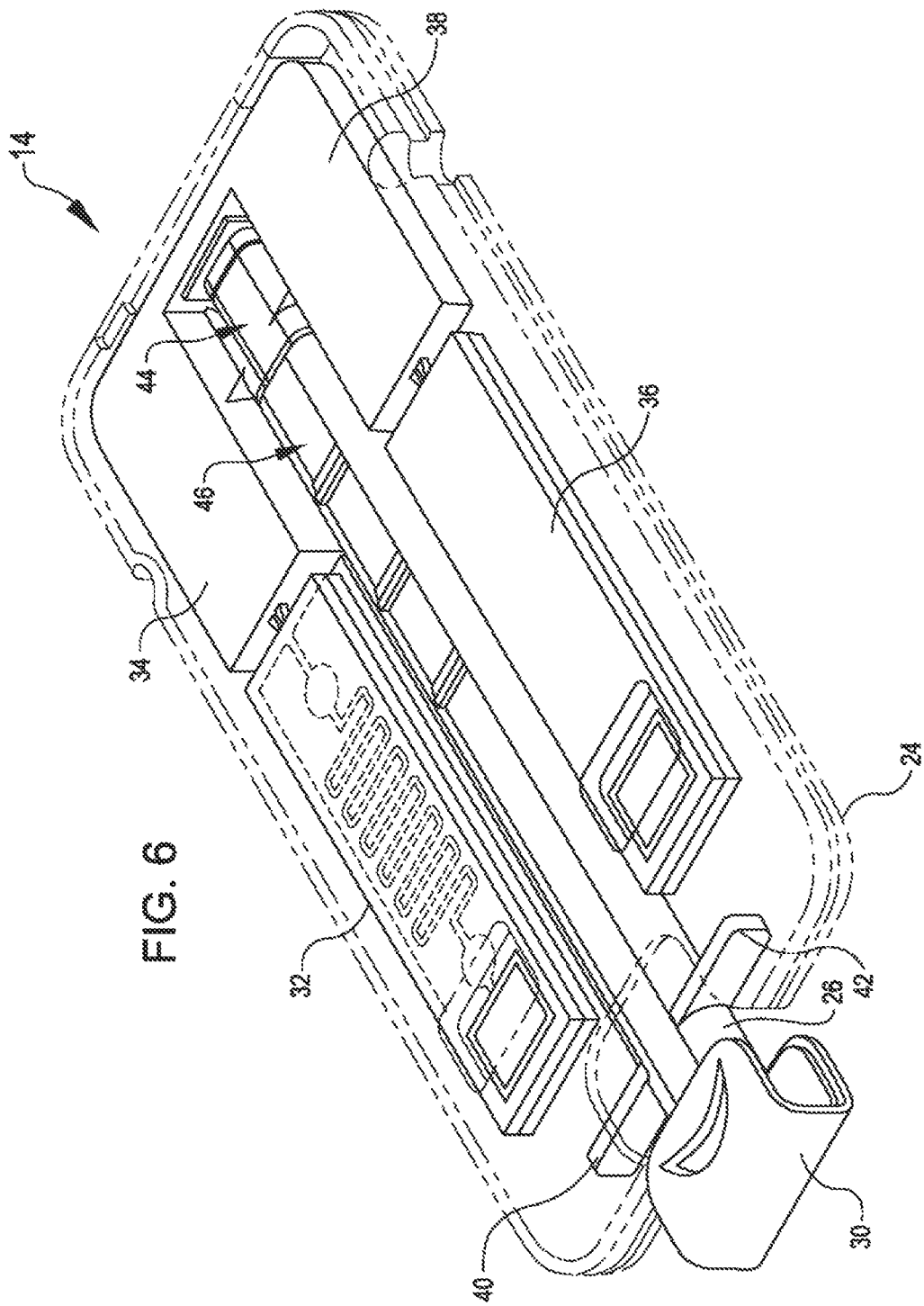
FIG. 6 shows internal components of the cartridge of the system of FIG. 1 in an isometric view with transparency, in accordance with embodiments.
Figure 7:
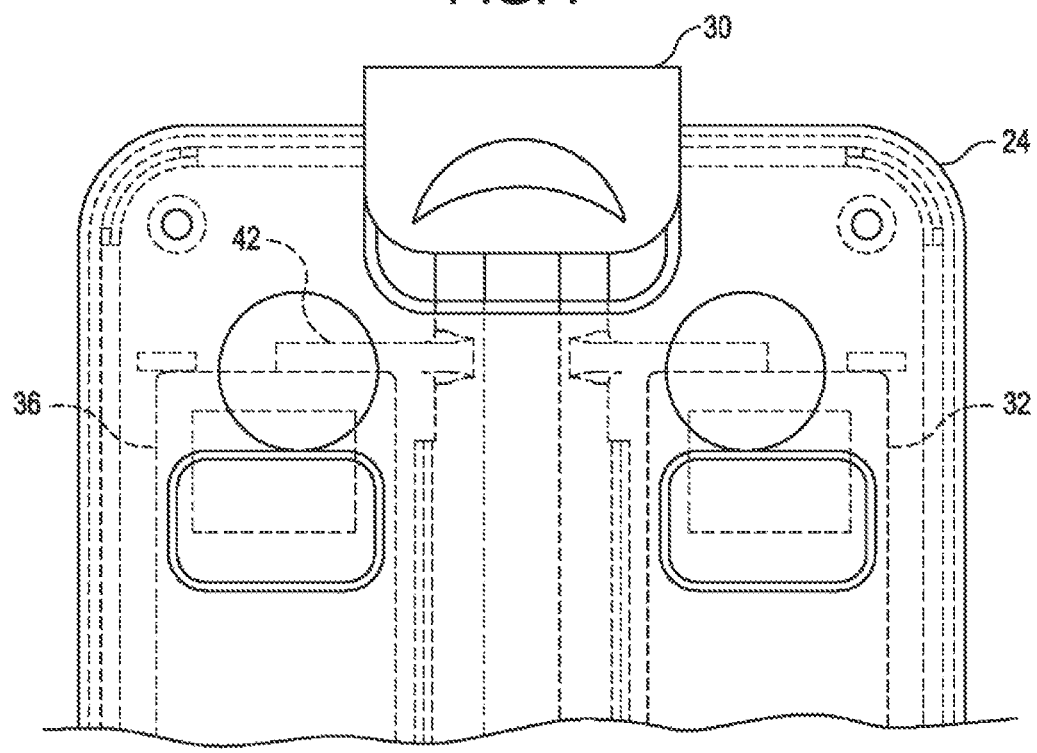
FIG. 7 shows a view of the cartridge of the system of FIG. 1 illustrating displacement of detection modules of the cartridge induced by induced motion of the swab tube, in accordance with embodiments.

FIG. 6 and FIG. 7 illustrate an induced reconfiguration of internal components of the cartridge 14 from a storage configuration to a ready-for-testing configuration. In the illustrated embodiment, the reconfiguration can be accomplished by a user-induced translation of the combination of the swab tube 26 and the swab tube cap 30 relative to the cartridge outer shell 24. The swab tube 26 is slidably mounted within the outer shell 24 to accommodate the induced translation of the swab tube 26 relative to the outer shell 24 to reconfigure the cartridge 14 from the storage configuration shown in FIG. 6 to the ready-to-use configuration (shown in FIG. 8). As shown in FIG. 6, the cartridge 14 includes a virus side (VS) detection module 32, a VS lysis module 34, a control side (CS) detection module 36, and a CS lysis module 38. Each of the VS detection module 32 and the CS detection module 36 is hermetically sealed in the storage configuration to preserve reagent components included therein prior to use of the cartridge 14. The VS detection module 32 is slidably mounted within the outer shell 24 to accommodate induced translation of the VS detection module 32 towards the VS lysis module 34 to fluidly couple the VS detection module 32 and the VS lysis module 34 during the reconfiguration of the cartridge 14 from the storage configuration to the ready-to-use configuration of the cartridge 14. Likewise, the CS detection module 36 is slidably mounted within the outer shell 24 to accommodate induced translation of the CS detection module 36 towards the CS lysis module 38 to fluidly couple the CS detection module 36 and the CS lysis module 38 during the reconfiguration of the cartridge 14 from the storage configuration to the ready-to-use configuration of the cartridge 14. As shown in FIG. 6 and FIG. 7, the swab tube 26 includes side extensions 40, 42 that engage the detection modules 32, 36 and push the detection modules 32, 36 into engagement with the lysis modules 34, 38 during induced translation of the swab tube 26 relative to the outer shell 24. Additionally, the cartridge 14 includes a hermetically sealed lysis buffer container 44 that contains a lysis buffer. During the induced translation of the swab tube 26 relative to the outer shell 24, a distal end 46 of the swab tube 26 creates an opening in the lysis buffer container 44, thereby releasing the lysis buffer into contact with the swab 28 to mix a portion of the biological sample on the swab 28 with the lysis buffer. In the illustrated embodiment, the outer shell 24 and the swab tube cap 30 have complementarily-shaped interfacing surfaces that engage when the swab tube 26 reaches the end of the induced translation relative to the outer shell 24 so as to fully enclose the swab tube 26 within the combination of the outer shell 24 and the swab tube cap 30, along with the rest of the internal components of the cartridge 14.

Figure 8:
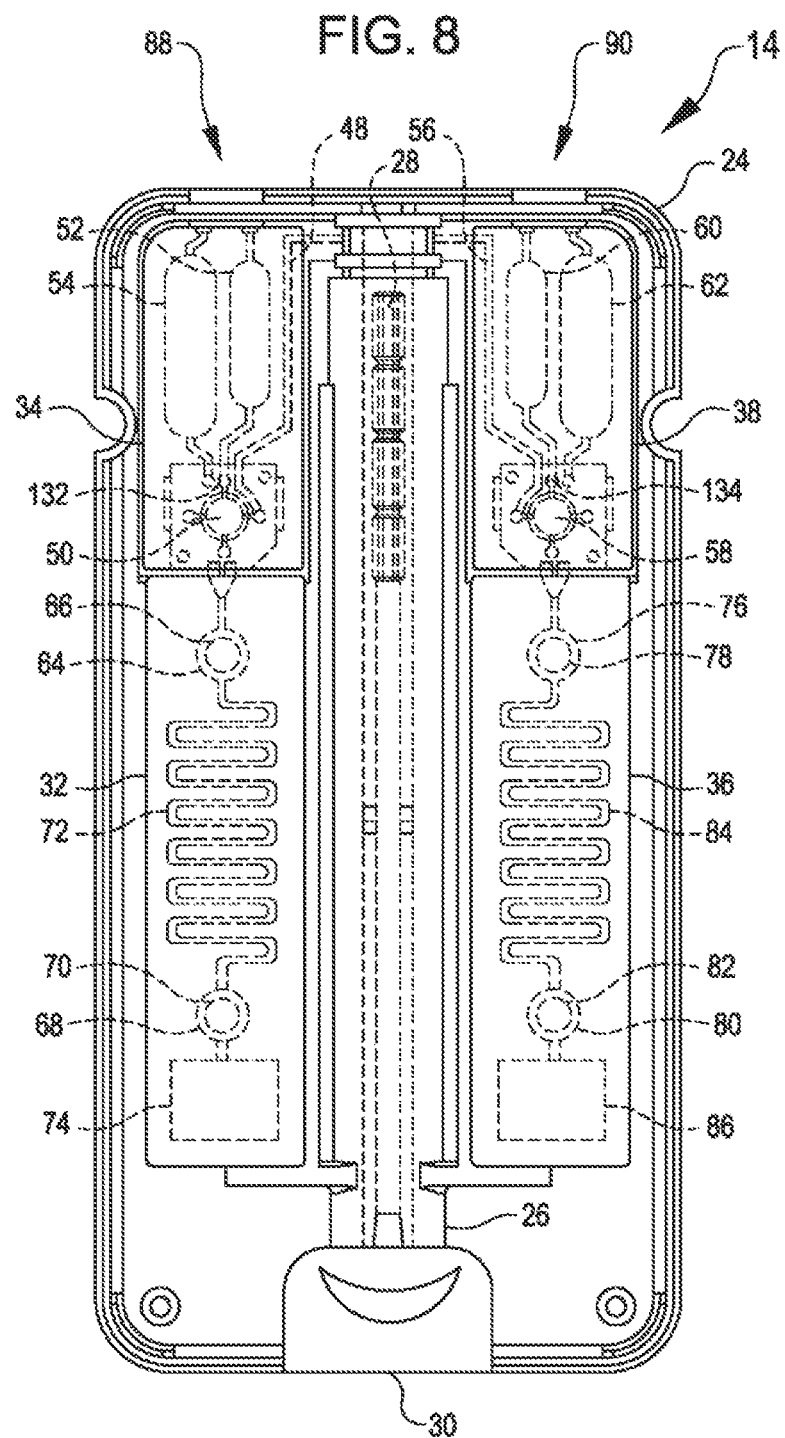
FIG. 8 shows internal components of the cartridge of the system of FIG. 1 in a top view with transparency, in accordance with embodiments.

FIG. 8 shows internal components of the cartridge 14. The internal components of the cartridge 14 include the outer shell 24, the swab tube 26, the swab tube cap 30, the VS detection module 32, the VS lysis module 34, the CS detection module 36, and the CS lysis module 38. Also shown in FIG. 8 is a sample swab 28 disposed within the swab tube 26 and enclosed within the swab tube 26 via the swab tube cap 30. The VS lysis module 34 includes a lysis transport tube 48, a lysis well 50, a vacuum chamber 52, a hydration water chamber 54. Similarly, the CS lysis module 38 includes a lysis transport tube 56, a lysis well 58, a vacuum chamber 60, a hydration water chamber 62. The VS detection module 32 includes an amplification cycle well 64, an amplification cycle reagent bead 66 disposed within the amplification cycle well 64, a detection cycle well 66, a detection cycle reagent bead 68 disposed within the detection cycle well 66, a transport conduit 72 fluidly connecting the amplification cycle well 64 and the detection cycle well 66, and a reading chamber 74. Similarly, the CS detection module 36 includes an amplification cycle well 76, an amplification cycle reagent bead 78 disposed within the amplification cycle well 76, a detection cycle well 80, a detection cycle reagent bead 78 disposed within the detection cycle well 80, a transport conduit 84 fluidly connecting the amplification cycle well 76 and the detection cycle well 80, and a reading chamber 86.

In the illustrated embodiment, the cartridge 14 includes a virus detection side 88 and a control detection side 90 suitable for use in detecting a target virus that requires the use of a control assay to validate the results produced by the virus detection processing. For example, a standard SARS-CoV-2 assay requires verification that the sample is correct to give a sensitive result with high precision. Accordingly, in addition to the processing accomplished via the virus detection side 88, an internal RNase P control check is accomplished via the control detection side 90 to determine whether the biological sample is suitable for a valid test for SARS-CoV-2. The processing of the biological sample accomplished via the control detection side 90 checks for the presence of suitable genetic material compatible with correct lysis of the biological sample and for the presence of human cells.

Figure 9:
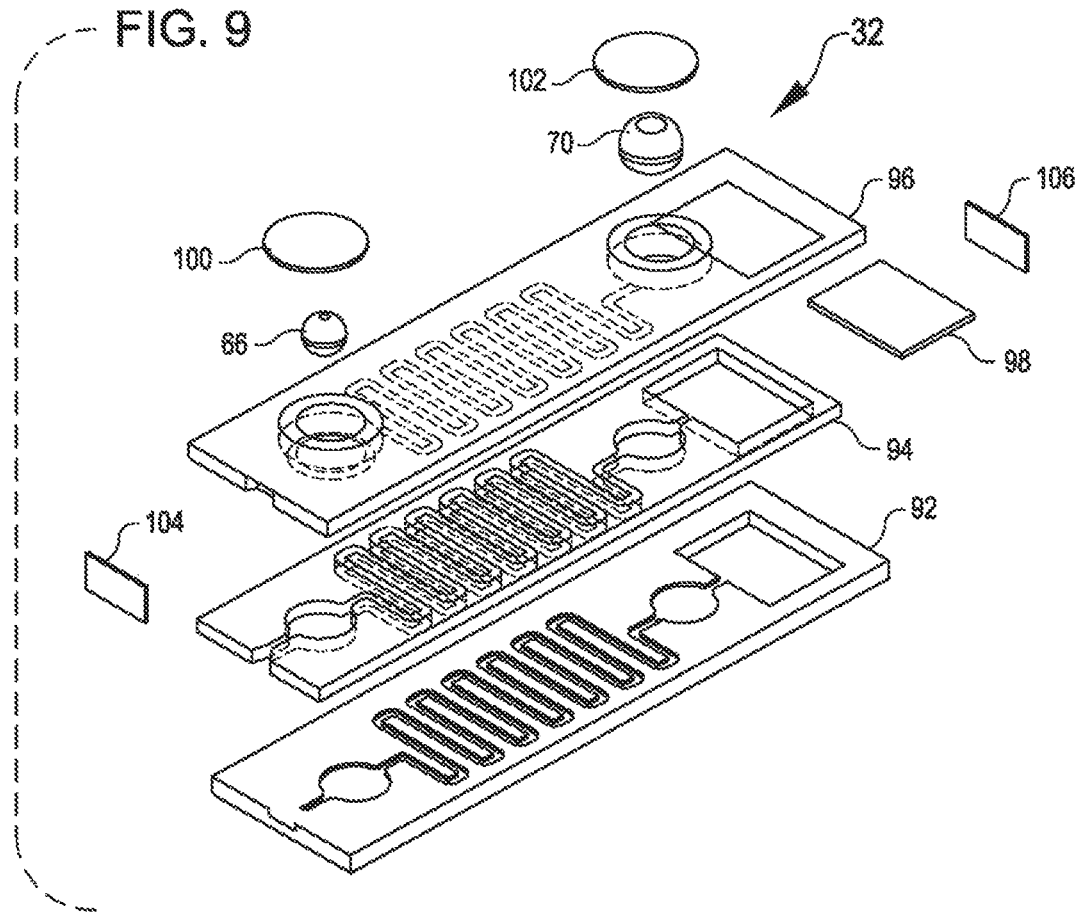
FIG. 9 shows details of a detection assembly of the cartridge of the system of FIG. 1 in an exploded isometric view, in accordance with embodiments.

FIG. 9 shows an exploded view the virus side detection module 32. The control side detection module 36 is configured the same as the virus side detection module 32 but for differences between the formulation of the reagent beads 66, 70, 78, 82. The virus side detection module 32 houses the reagent beads 66, 70 in a watertight manner so as to isolate the reagent beads 66, 70 from external conditions in the storage configuration of the cartridge 14. Likewise, the control side detection module 36 houses the reagent beads 78, 82 in a watertight manner so as to isolate the reagent beads 78, 82 from external conditions in the storage configuration of the cartridge 14. The virus side detection module 32 is a microfluidic assembly formed of a closure member 92, a central member 94, a reagent bead lid member 96, the absorption and reading pad 98, the virus side activation cycle reagent bead 66, the virus side detection cycle reagent bead 70, closure disks 100, 102, a pre-use input side isolation membrane 104, and a pre-use output side isolation membrane 106. The virus side detection module 32 can be formed from any suitable materials. For example, the closure member 92, the central member 94, and the reagent bead lid member 96 can be formed from a suitable plastic.

The closure member 92 and the central member 94 can be integrally formed using any suitable approach, such as via injection molding. The absorption and reading pad 98 can be made mainly of cellulose fiber paper, glass fibers, or other suitable materials, as long as the material does not affect the fluorescence measurements. The virus side detection module 32 forms the virus side activation cycle well 64 and the virus side detection cycle well 68, which can have any suitable shape, such as cylindrical. The closure disks 100, 102 can be formed of any suitable material (e.g. a suitable plastic, a plasticized aluminum foil, a flanged plastic plug) and attached to the reagent bead lid member 96 in any suitable manner (e.g., fusing, sliding door) to enclose the reagent beads in the wells 64, 68. The pre-use input side isolation membrane 104 and the pre-use output side isolation membrane 106 can be formed from any suitable material (e.g., an aluminum sheet). The pre-use input side isolation member 104 is installed at the inlet end of the virus side detection module 32. The pre-use output side isolation member 106 is installed over a vent that vents the reading chamber 74 during movement of the fluids in the virus side detection module 32. The pre-use isolation membranes 104, 106 can be made from any suitable material and attached using any suitable approach. The pre-use isolation membranes 104, 106 block the fluid pathways of the virus side detection module 32 to isolate the reagent beads 66, 70 from the external environment prior to use of the cartridge 14.

The exterior of the cartridge 14 is shown in FIG. 3. In the illustrated embodiment, the exterior of the cartridge 14 was designed so as to avoid sharp edges where possible and dimensioned facilitate holding of the cartridge 14 in one hand. The cartridge 14 contains and encloses the reagents and fluids for isothermal amplification reactions and their detection.

The cartridge 14 can be fabricated from any suitable combination of suitable materials. For example, suitable materials from which the cartridge 14 can be made include, but are not limited to, polypropylene, polycarbonate, polystyrene, polyurethane, polyethylene, polyacrylate, polymethacrylate, polymethylmethacrylate, other acrylic, polyvinylchloride, acrylonitrile-butadiene-styrene, poly(ethylene terephthalate), polytetrafluoroethylene, nylon, a co-polymer, or combinations thereof.

Figure 10:
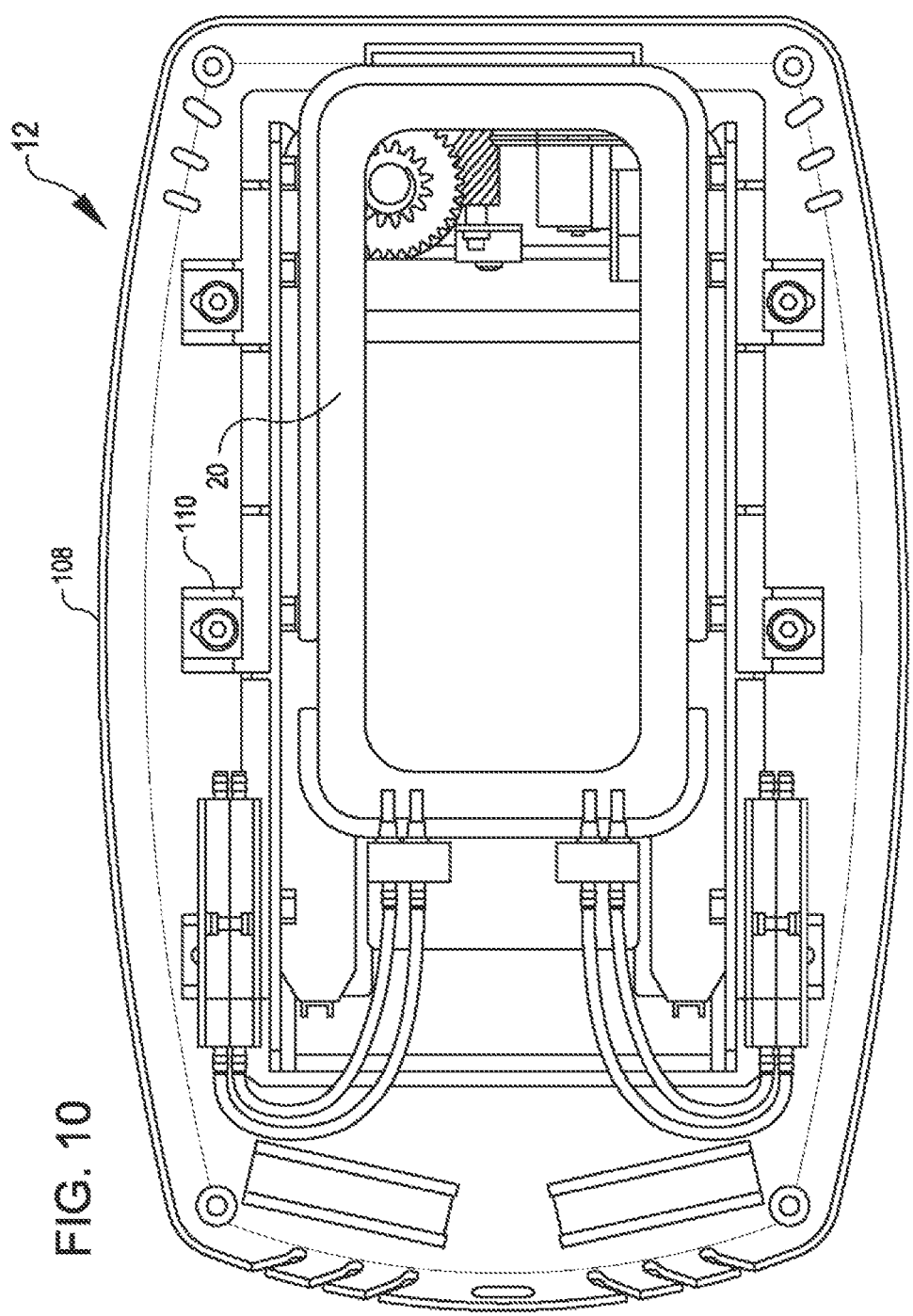
FIG. 10 shows internal components of the analysis device of the system of FIG. 1 in a top view with transparency, in accordance with embodiments.
Figure 11:
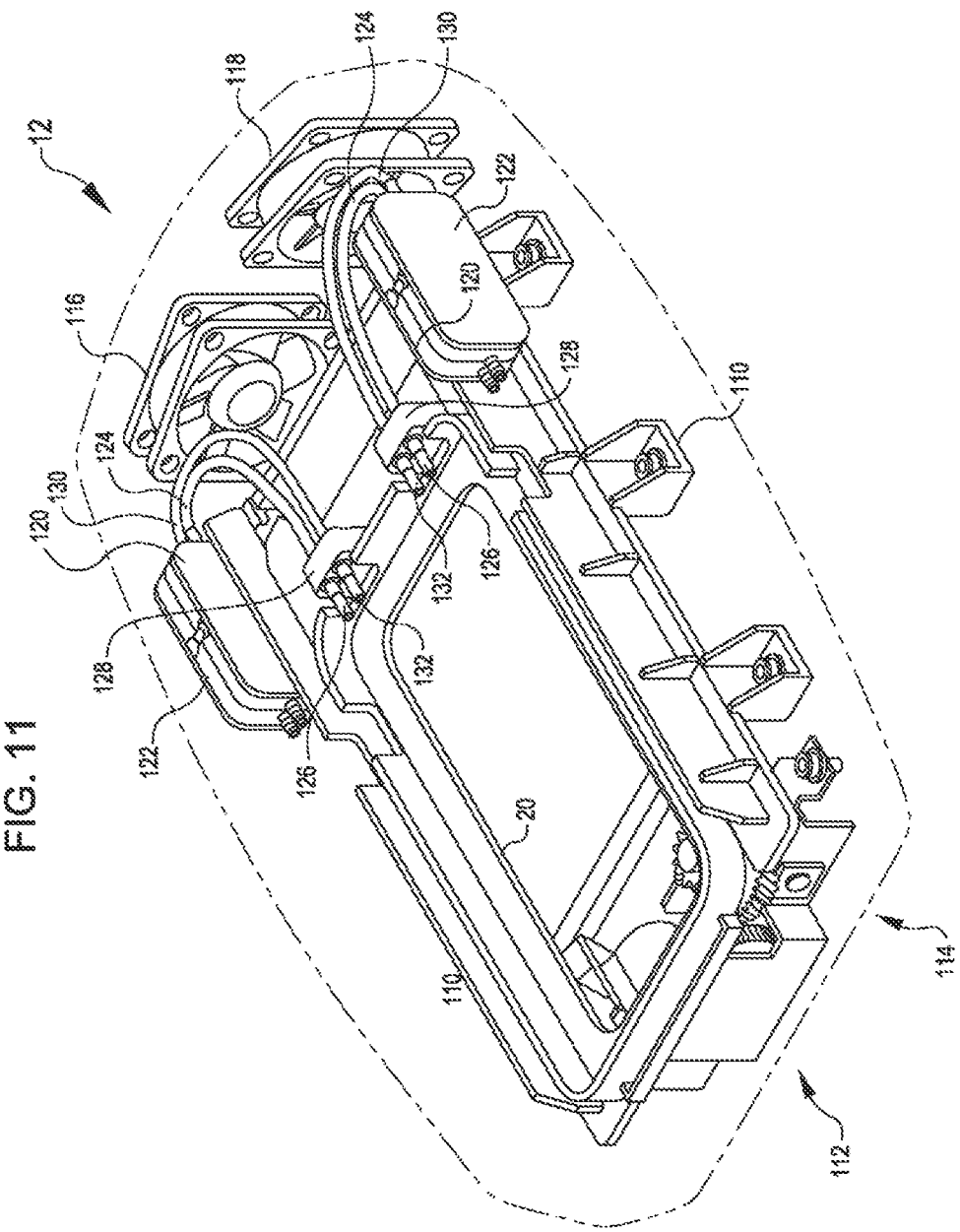
FIG. 11 shows internal components of the analysis device of the system of FIG. 1 in an isometric view with transparency, in accordance with embodiments.

FIG. 10 and FIG. 11 show internal components of the analysis device 12. The analysis device 12 includes a two-part housing assembly 108, a support frame 110 attached to the housing 108, a cartridge handling assembly 112, a controller, detection optics, a fluid displacement assembly, a cooling system, and a communication assembly. The cartridge handling assembly 112 is attached to the support frame 110. The cartridge handling assembly 112 includes the cartridge support 20 and a cartridge input mechanism 114. The cartridge handling assembly 112 includes a locking mechanism operable to prevent ejection of the cartridge 14 prior to cooling of the cartridge 14 below an acceptable temperature. In the illustrated embodiment, the cartridge input mechanism 114 includes a gear train driven by a stepper motor that is controlled by the controller to control the input speed of the cartridge 14. In some embodiments, the controller monitors the electric power supplied to the stepper motor and stops operation of the stepper motor in response to the electric power supplied to the stepper motor exceeding a suitable electric power limit for the cartridge input mechanism 114. As an alternative to the illustrated cartridge input mechanism 114, a manually operated cartridge input mechanism can be used. For example, such a manually operated cartridge input mechanism can include a push operated cartridge input mechanism including a cartridge support that can be manually repositioned from an extended position for loading and unloading a cartridge and an retracted position in which the cartridge is operatively coupled with the analysis device 12.

The cooling system is attached to the support frame 110 and includes fans 116, 118. The fans 116, 118 are controlled by the controller. The fans 116, 118 are operable to draw a cooling flow of air through the housing to cool the cartridge 14 and internal components of the analysis device 12.

In many embodiments, the analysis device 12 includes a battery for powering operation of the analysis device 12. In some embodiments, the battery is capable of powering the analysis device 12 for at least 2 continuous tests. The analysis device can also be connected to an external power supply to receive electrical power to power operation of the analysis device.

The fluid displacement assembly includes two pumps attached to the support frame 110 and configured for moving fluid within each of the two sides 88, 90 of the cartridge 14. Each of the two pumps includes a positive displacement pump 120 and a vacuum pump 122. A hose 98 extends from each of the positive displacement pumps 120 to a nozzle 126 supported by a respective one of two supports 102. Likewise, a hose 104 extends from each of the vacuum pumps 122 to a nozzle 132 supported by a respective one of the two supports 102. Each of the nozzles of the two pairs of nozzles 126, 132 is configured to penetrate into a mating orifice of the cartridge 14 during insertion of the cartridge 14 into the analysis device 12 to place the respective pump in fluid communication with a respective conduit within the cartridge 14. In many embodiments, each of the mating orifices of the cartridge 14 are covered by a membrane to prevent entry of any unwanted substance into the cartridge through the mating orifices prior to use of the cartridge 14. During insertion of the cartridge 14 into the analysis device, each nozzle of the two pairs of nozzles 126, 132 penetrates through the respective protective membrane. In many embodiments, a respective one-way valve is coupled with each nozzle of the two pairs of nozzles 126, 132 to prevent the backflow of displaced liquids and to enable increased precision in the operation of the cartridge 14.

The analysis device 12 can be fabricated from any suitable combination of suitable materials. For example, suitable materials from which the analysis device 12 can be constructed include, but are not limited to, suitable plastics, polymers, rubbers, metals, composites or any other suitable materials.

The analysis device 12 and the cartridge 14 can be adapted for testing for the presence of more than one virus in the biological sample. For example, the virus detection side 88 components of the cartridge 14 can be replicated any suitable number of times within the cartridge 14. Likewise, the control detection side 90 components of the cartridge 14 can be replicated any suitable number of times within the cartridge. Similarly, the analysis device 12 can be adapted to operate any resulting configuration of the cartridge 14 for testing for the presence of more than one virus in the biological sample.

Operational Sequence

Figure 13:
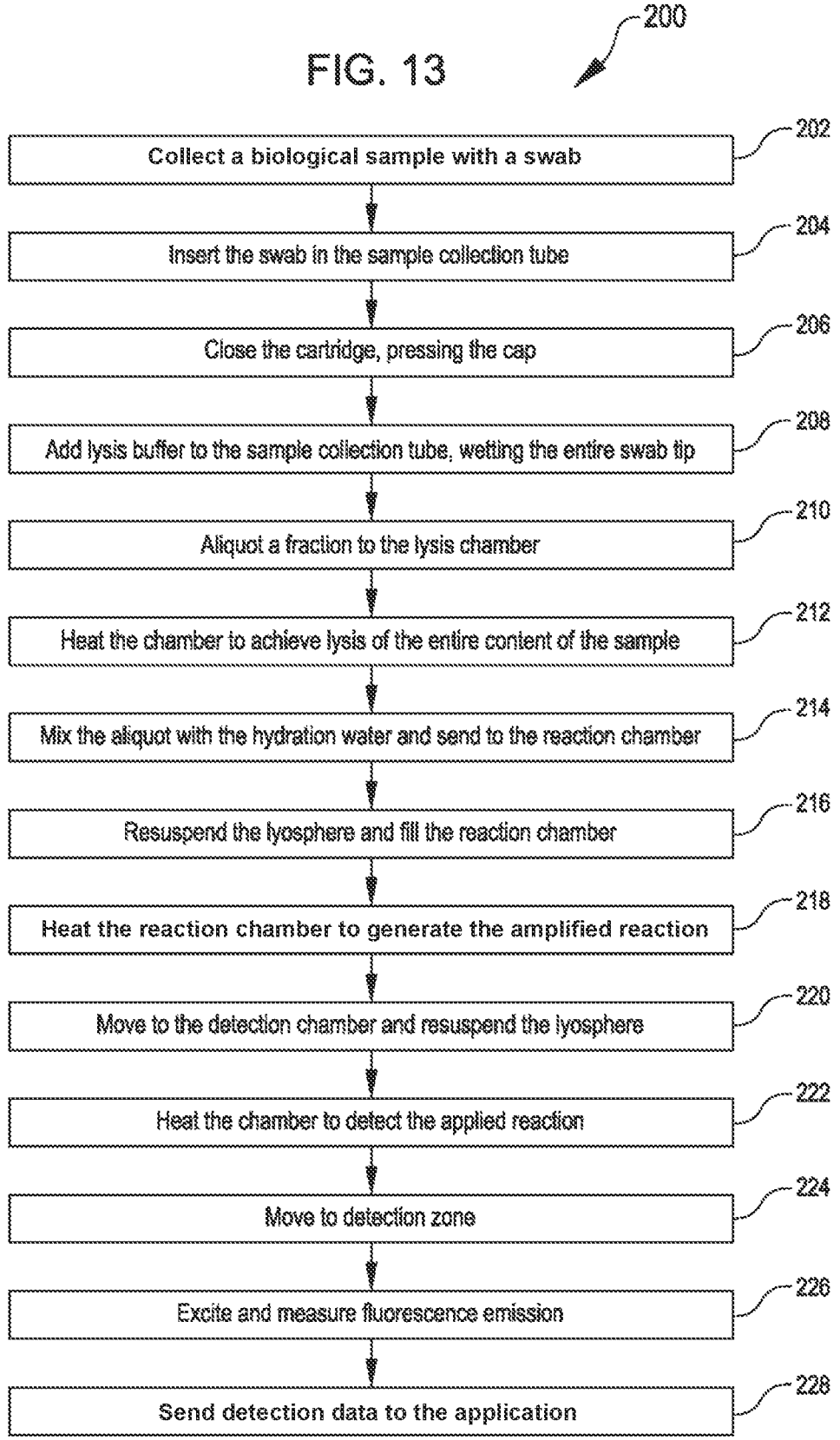
FIG. 13 shows a simplified schematic diagram of an approach for detecting whether a target virus is present in a biological sample, in accordance with embodiments.

FIG. 13 is a simplified schematic diagram of acts of a process 200 for testing a biological sample for the presence of a target virus, in accordance with embodiments. Some or all of the process 200 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

While the process 200 can be accomplished using the system 10 and is described herein in the context of using the system 10, the process 200 can be performed using any suitable devices and/or systems. In act 202, a biological sample to be tested for the presence of a target virus is collected. The biological sample for analysis can be obtained by taking a nasal or nasopharyngeal sample, with the appropriate procedure in both nostrils, using the swab 28. The sample must be taken correctly because it must contain material suitable for the control. With the fresh sample, the swab 28 is inserted into the swab tube 26 to the bottom of the swab tube 26 (act 204). Preferably, the cartridge 14 is held in a vertical orientation so that the swab 28 is inserted downward into the swab tube 26. The cartridge 14 can, however, be held in a horizontal orientation during insertion of the swab 28 because the fluids in the cartridge 14 are contained against escape from the cartridge 14. The swab 28 is then broken at the breaking point of the swab 28 and the remaining handle is discarded. Continuing to press the cap 30 is used to translate the swab tube 26 relative to the housing 24 to reconfigure the cartridge 14 from the storage configuration to the ready-to-use configuration (act 206). The reconfiguration of the cartridge 14 from the storage configuration to the ready-to-use configuration releases the lysis buffer into the swab tube 26 thereby wetting the swab 28 (act 208).

To start an analysis of a biological sample, the analysis device 12 can be connected to a source of electrical power, which will activate the analysis device 12 and, if necessary, will start charging the battery. When connected to the source of electrical power, the start button 22 will illuminate to indicate that the analysis device 12 is ready to process a cartridge 14. In response to pressing of the start button 22, the controller operates the cartridge input mechanism 114 to reconfigure the analysis device 12 from the closed configuration shown in FIG. 2 to the open configuration shown in FIG. 3.

In the open configuration, the analysis device 12 is ready for the insertion of a cartridge 14 (in the ready-to-use configuration with a sample swab 28 with a biological sample to be tested contained thereon enclosed within the swab tube 26) is placed within the cartridge support 20. With the cartridge 14 disposed in the cartridge support 20, pressing the start button 22 will cause the controller to operate the cartridge input mechanism 114 to insert the cartridge 14 into the analysis device 12. During the insertion of the cartridge 14 into the analysis device 12, the cartridge 14 is operationally coupled with the fluid displacement assembly as discussed above. In many embodiments, the cartridge 14 includes flexible seals, each with a controlled opening through which each nozzle of the pairs of nozzles 126, 132 is inserted, thereby ensuring a fluid tight seal to avoid fluid leakage.

In many embodiments, the analysis device 12 induces vibration of the swab tube 26 to enhance release of the biological sample on the swab 28 into the lysis buffer. The analysis device 12 can include any suitable mechanism for inducing the vibration of the swab tube 26. For example, the analysis device 12 can include a high-frequency vibrating motor that applies vibration to the end of the swab tube 26 at which the biological sample is disposed, an ultrasound transducer that emits ultrasound onto the swab tube 26, or any suitable mechanism that agitates the lysis buffer surrounding the swab 28.

Following the induced vibration of the swab tube 26 by the analysis device 12, the controller operates the virus side vacuum pump 122 to reduce the pressure within the vacuum chamber 52, the lysis well 50, and the lysis transport tube 48, thereby drawing a portion of the combined lysis buffer and biological sample from the swab tube 26, through the lysis transport tube 48, to fill the lysis well 50 (act 210). The vacuum chamber 52 is in fluid communication with the lysis well 50 through a one-way valve 132. The valve 132 can be made of plastic sheets, although a slide valve or the like can be used. The vacuum generated by the virus side vacuum pump 122 initially transfers the portion of the combined lysis buffer and biological sample into the lysis well 50. When the lysis well 50 is full, the combined lysis buffer and biological sample then begins to advance into the vacuum chamber 52, where an electronic front control stops movement of the combined lysis buffer and biological sample via by electronically stopping the vacuum pump 122. Once this first cycle is completed, the lysis well filling sequence is repeated on the control side. Each side of the cartridge 14 has differential activation of the vacuum pumps 122 to avoid interference problems. The controller operates the control side vacuum pump 122 to reduce the pressure within the vacuum chamber 60, the lysis well 58, and the lysis transport tube 56, thereby drawing a portion of the combined lysis buffer and biological sample from the swab tube 26, through the lysis transport tube 56, to fill the lysis well 58. The vacuum chamber 60 is in fluid communication with the lysis well 58 through a one-way valve 134. The valve 134 can be made of plastic sheets, although a slide valve or the like can be used. The vacuum generated by the control side vacuum pump 122 initially transfers the portion of the combined lysis buffer and biological sample into the lysis well 58. When the lysis well 58 is full, the combined lysis buffer and biological sample then begins to advance into the vacuum chamber 60, where an electronic front control stops movement of the combined lysis buffer and biological sample via by electronically stopping the control side vacuum pump 122.

Figure 12:
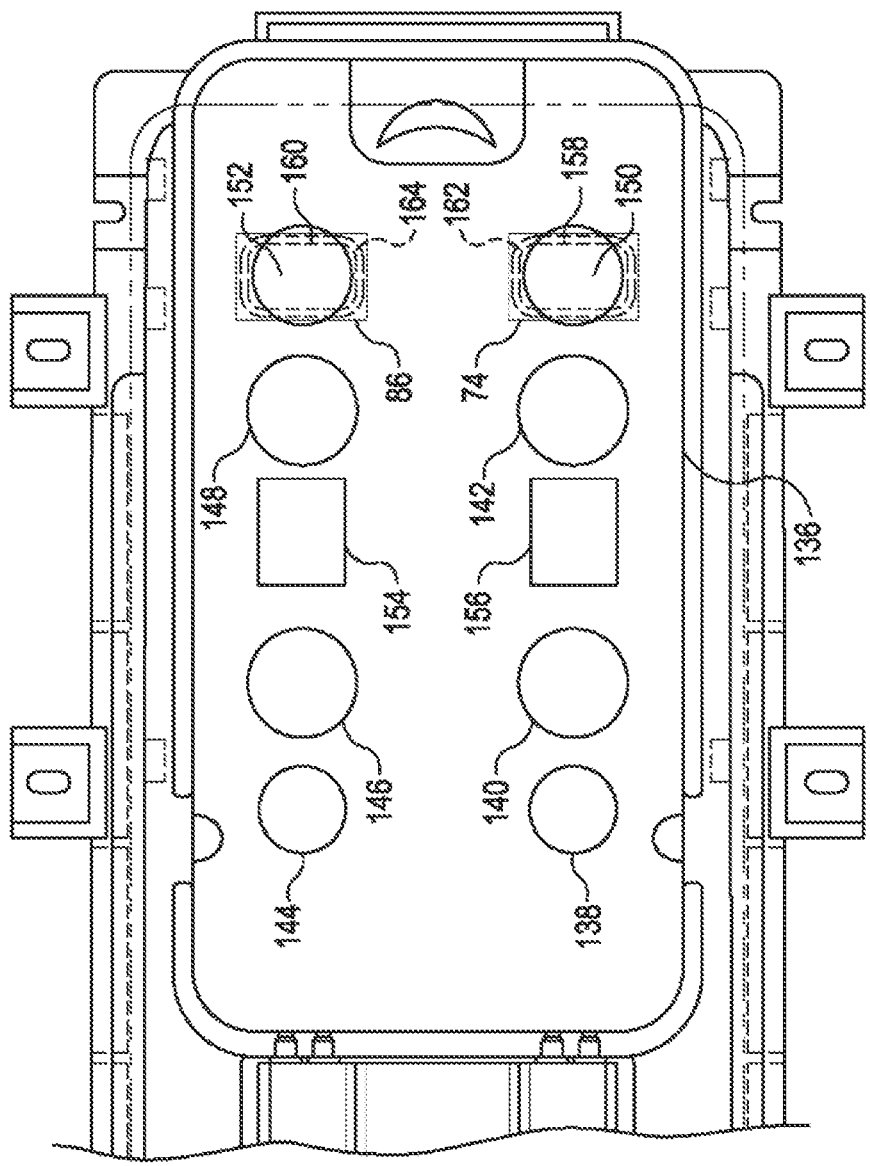
FIG. 12 shows locations of heating and reading zones of the cartridge of the system of FIG. 1 in a top view with transparency, in accordance with embodiments.

With both lysis wells 50, 58 filled with combined lysis buffer and biological sample, a warm-up cycle begins. The analysis device 12 includes a controller in the form of a controller printed circuit board (PCB) 107 (shown in FIG. 12). The controller PCB 136 includes 6 attached heating elements 138, 140, 142, 144, 146, 148, two reading zones 120, 122, and two refrigeration elements 154, 156. The combined lysis buffer and biological sample in each of the lysis wells 50, 58 is heated to within a suitable temperature range and maintained in the temperature range for a suitable period of time to accomplish proper lysis of the biological sample (act 212). For example, in some embodiments, the controller PCB operates heating elements 138, 144 to heat the combined lysis buffer and biological sample in the lysis wells 50, 58 to 95° C. for a period of 5 to 10 min. The controller PCB 136 includes temperature sensors for monitoring the temperature of the combined lysis buffer and biological sample in each of the lysis wells 50, 58.

At the end of the lysis period, the positive displacement pumps 120, which are connected by the nozzles 132 to a respective one of the hydration chambers 54, 60, are activated by the controller PCB 136 to pump hydration water from each of the respective hydration chambers 54, 60, through one-way valves 132, 134, into the lysis chambers 48, 56. The pumping action of the positive displacement pumps 120 transfers a combination of the hydration water and the post-lysis combined lysis buffer and biological sample in each of the lysis wells 50, 58 through respective one way valves 132, 134 and into the activation cycle wells 64, 76 (act 214). When the virus side activation cycle well 64 is full, the combination of hydration water and the post-lysis combined lysis buffer and biological sample then begins to advance into the transport conduit 72, where an electronic front control stops operation of the virus side positive displacement pump 120. Likewise, when the control side activation cycle well 76 is full, the combination of hydration water and the post-lysis combined lysis buffer and biological sample then begins to advance into the control side transport conduit 84, where an electronic front control stops operation of the control side positive displacement pump 120. The presence of the hydration water in the virus side activation cycle well 64 rehydrates the virus side activation cycle reagent bead 66. Likewise, the presence of the hydration water in the control side activation cycle well 76 rehydrates the control side activation cycle reagent bead 78 (act 216).

With the resulting liquid in each of the virus side activation cycle well 64 and control side activation cycle well 76, the controller PCB 136 operates the heating elements 140, 146 to heat the resulting liquid in the activation cycle wells 64, 76 to within a suitable temperature range and maintained in the temperature range for a suitable period of time to accomplish the activation cycle (act 218). For example, in some embodiments, the controller PCB 136 operates the heating elements 140, 146 to heat the resulting liquid in the activation cycle wells 64, 76 to 65° C. for a period of 20 to 45 minutes. To avoid premature resuspension of the detection cycle beads 70, 82 in the detection cycle wells 68, 80 during the activation cycle, each of the transport conduits 72, 84 is configured as a labyrinth to inhibit transport of water vapor to the detection cycle wells 68, 80 during the activation cycle heating of the liquid in the activation cycle wells 64, 76. The refrigeration elements 154, 156 are configured for cooling of vapor within the transport conduits 72, 84 and the controller PCB 136 operates the refrigeration elements 154, 156 during the activation cycle to further inhibit transport of water vapor to the detection cycle wells 68, 80.

At the end of the activation cycle period, the controller PCB 136 operates the positive displacement pumps 120 to transfer the resulting reaction fluid in the activation cycle wells 64, 76 to the detection cycle wells 68, 80 through the transport conduits 72, 84. In some embodiments, each of the detection cycle beads 68, 78 is degraded when heated to an excess temperature so the controller PCB 136 operates the refrigeration element to cool reaction fluid to a suitable temperature during the conveyance of the reaction fluid through the transport conduits 72, 84 from the activation cycle wells 64, 76 to the detection cycle wells 68, 80 (act 220). For example, the controller PCB 136 can operate the refrigeration element to cool the reaction fluid to 35° C., which in some embodiments is a suitable temperature for hydration of the detection cycle beads 68, 78. In some embodiments, the controller PCB 136 operates the heating elements 142, 148 to maintain the liquid in the detection cycle wells 68, 80 at a constant temperature of 35° C. for a period of 5 to 10 minutes for resuspension of the detection cycles beads 68, 78 (act 222).

Following resuspension of the detection cycle beads 68, 78, the controller PCB 136 operates the positive displacement pumps 120 to push the resulting detection liquid from the detection cycle wells 68, 80 to the reading chambers 74, 86 (act 224). In some embodiments, the analysis device 12 includes an absorption and reading pad 98 housed in each of the reading chambers 74, 86.

In act 226, fluorescence emission from the detection liquid in the reading chambers 74, 86 is excited and measured. The analysis device 12 includes excitation light emitters 158, 160 and fluorescence light detectors 162, 164 for exciting and reading resulting fluorescence of the resulting detection liquid in each of the reading chambers 74, 86. Each of the excitation light emitters 158, 160 can include a suitable light emitting diode (LED) controlled by the controller PCB 136. Each of the fluorescence light detectors 162, 164 can include a suitable light detecting resistor (LDR) that generates and supplies a fluorescence detection signal to the controller PCB 136. The controller PCB 136 can control the excitation light emitters 158, 160 and the fluorescence light detectors 162, 164 to take a reading of the absorption and reading pad 98 prior to the transfer of the resulting detection fluid into the reading chambers 74, 86 for use as a reference that is used to enable a more robust and comparable measurement. In some embodiments, the excitation light emitters 158, 160 emit light in the blue range (e.g., 470 nm wavelength). In some embodiments, the analysis device 12 includes one or more blue optical filters to limit the wavelength(s) of the excitation light that reaches the resulting detection fluids in the reading chambers 74, 86. In some embodiments, the resulting detection fluid in the reading chambers 74, 86 emits a fluorescence in the with a wavelength of about 520 nm. In some embodiments, the analysis device 12 includes one or more amber optical filters to limit the wavelength(s) of the light that reaches the fluorescence light detectors 162, 164 to green light between 500 and 550 nm.

In some embodiments, the controller PCB 136 processes output signals of the fluorescence light detectors 162, 164 to quantify the detected fluorescence (virus side and control side) and determine a detection result regarding whether the target virus is detected in the biological sample. In many embodiments, the detection result is one of a positive result (indicating presence of the target virus in the biological sample), a negative detection (indicating absence of the target virus in the biological sample), or an invalid result (indicating insufficiency of the biological sample for determining whether the target virus is present in the biological sample). In some embodiments, the controller PCB 136 controls a communication assembly to wirelessly transmit the detection result to the electronic device 16 for communication to a user (act 228). In some embodiments, the controller PCB 136 controls the communication assembly to wirelessly transmit a notification to the electronic device 16 that informs the user of the end of the test. In some embodiments, the controller PCB 136 controls the communication assembly to wirelessly transmit fluorescence data (which quantifies the output signals of the fluorescence light detectors 162, 164) to the electronic device and the electronic device processes the fluorescence data to determine the detection result regarding whether the target virus is detected in the biological sample.

In many embodiments, the controller PCB 136 controls the cooling fans 116, 118 to cool the cartridge 14 down following the detection of the fluorescence readings. The cooling fans 116, 118 can be operated over any suitable portion of the test cycle, including throughout all of the test cycle. Following the detection of the fluorescence readings, the cooling fans 116, 118 can be operated at a high speed to reduce the temperature of the cartridge 14 to a level suitable for ejection of the cartridge 14 from the analysis device 12. In many embodiments, the analysis device 12 prevents ejection of the cartridge 14 prior to the temperature of the cartridge being reduced down to the suitable level.

Analysis Device Control Sequence

Figure 14:
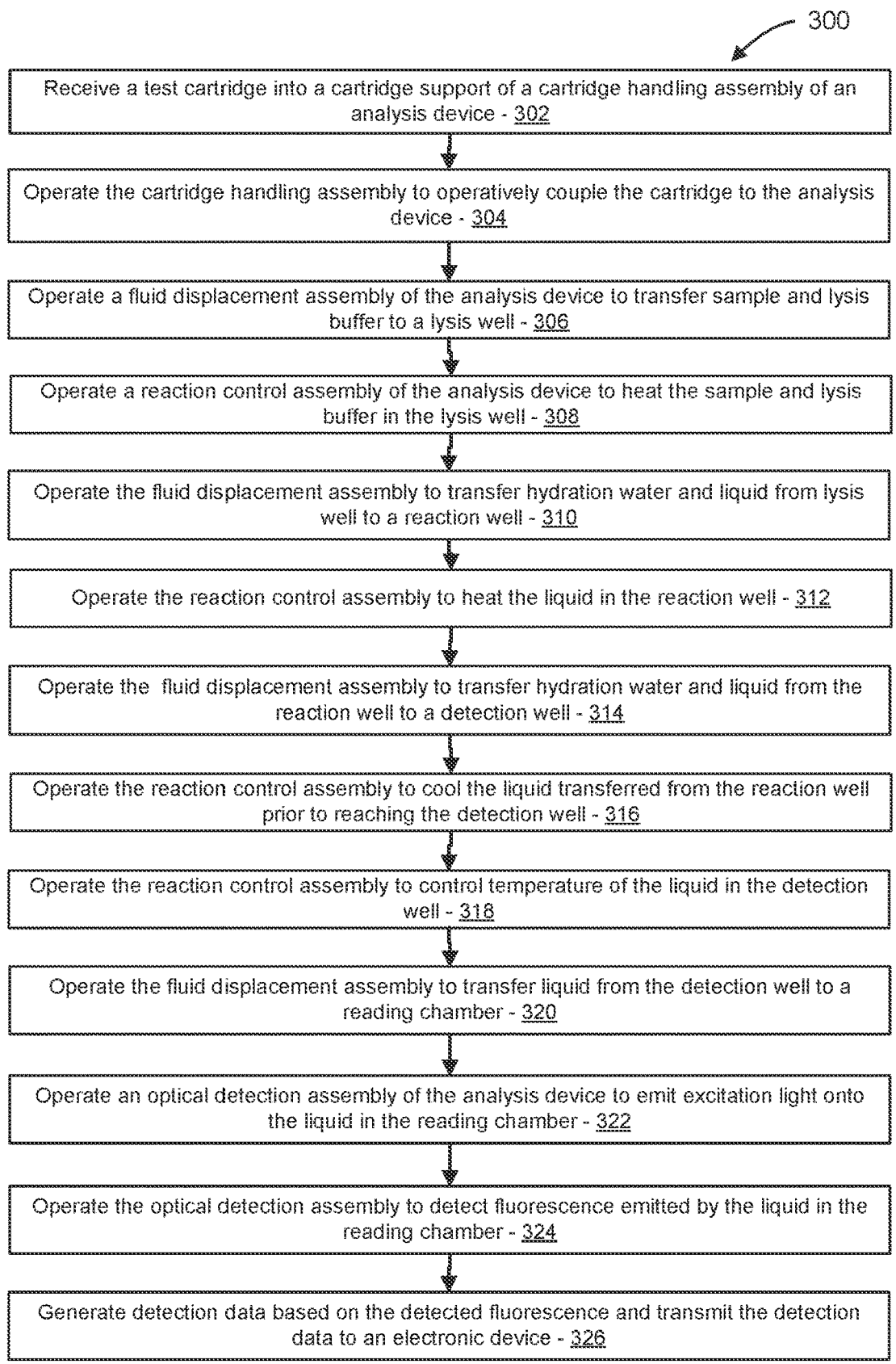
FIG. 14 shows a simplified schematic diagram of an approach for operating an analysis device to operate a cartridge to detect whether a target virus is present in a biological sample, in accordance with embodiments.

FIG. 14 is a simplified schematic diagram of acts of a process 300 for controlling operation of an analysis device to operate a cartridge to test whether a biological sample within a cartridge contains a target virus, in accordance with embodiments. Some or all of the process 300 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

While the process 300 can be accomplished using the system 10, the process 300 can be performed using any suitable devices and/or systems. In act 302, a cartridge is received into a cartridge support of a cartridge handling assembly of an analysis device. In act 304, the cartridge handling assembly is operated to operatively couple the cartridge to the analysis device. In act 306, a fluid displacement assembly is operated to transfer sample and lysis buffer to a lysis well. In act 308, a reaction control assembly is operated to heat the sample and the lysis buffer in the lysis well. In act 310, the fluid displacement assembly is operated to transfer hydration water and liquid from the lysis well to a reaction well. In act 312, the reaction control assembly is operated to heat the liquid in the reaction well. In act 314, the fluid displacement assembly is operated to transfer hydration water and liquid from the reaction well to a detection well. In act 316, the reaction control assembly is operated to cool the liquid transferred from the reaction well prior to reaching the detection well. In act 318, the reaction control assembly is operated to control the temperature of the liquid in the detection well. In act 320, the fluid displacement assembly is operated to transfer liquid from the detection well to a reading chamber. In act 322, an optical detection assembly is operated to emit excitation light onto the liquid in the reading chamber. In act 324, the optical detection assembly is operated to detect fluorescence emitted by the liquid in the reading chamber. In act 326, detection data is generated based on the detected fluorescence and transmitted to an electronic device.

Figure 15:
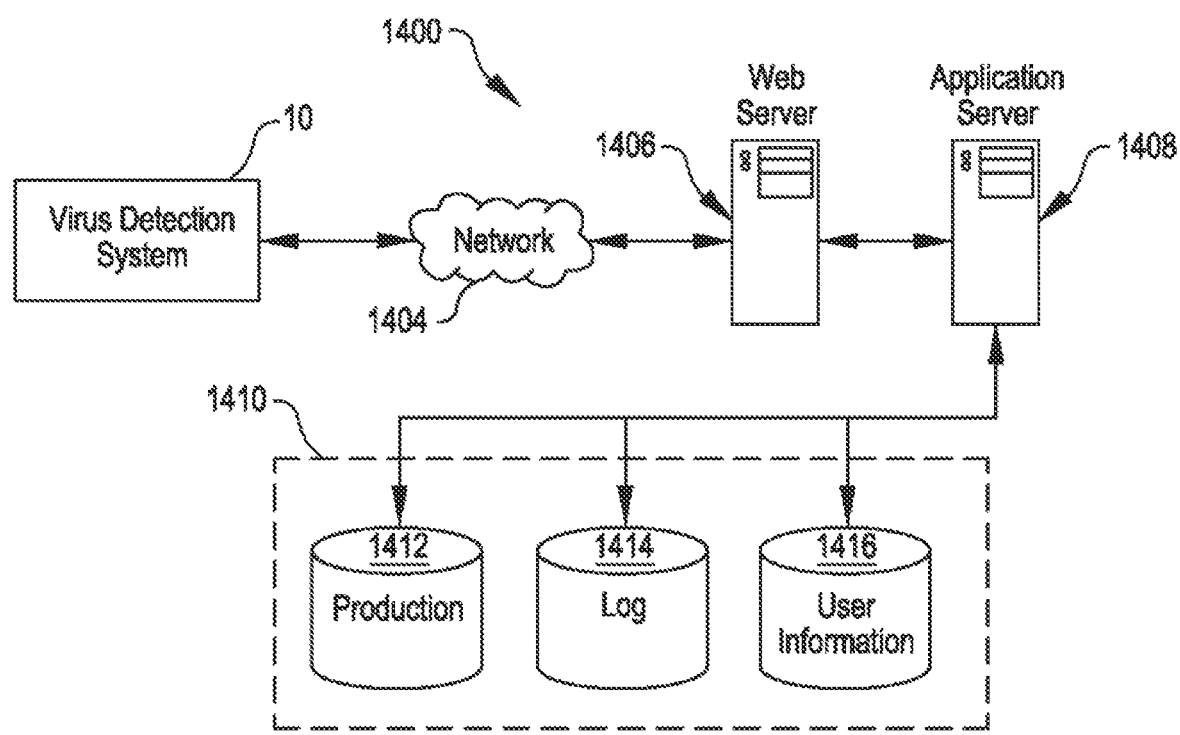
FIG. 15 illustrates an environment in which various embodiments can be implemented.

FIG. 15 illustrates an environment in which various embodiments can be implemented.

FIG. 15 illustrates aspects of an example environment 1400 for implementing aspects in accordance with various embodiments. As will be appreciated, although a Web-based environment is used for purposes of explanation, different environments may be used, as appropriate, to implement various embodiments. The environment includes the virus detection system 10, which can include any appropriate device operable to send and receive requests, messages, or information over an appropriate network 1404 and convey information back to a user of the device. Examples of such client devices include personal computers, cell phones, handheld messaging devices, laptop computers, set-top boxes, personal data assistants, electronic book readers, and the like. The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. In this example, the network includes the Internet, as the environment includes a Web server 1406 for receiving requests and serving content in response thereto, although for other networks an alternative device serving a similar purpose could be used as would be apparent to one of ordinary skill in the art.

The illustrative environment includes at least one application server 1408 and a data store 1410. It should be understood that there can be several application servers, layers, or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. The application server can include any appropriate hardware and software for integrating with the data store as needed to execute aspects of one or more applications for the client device, handling a majority of the data access and business logic for an application. The application server provides access control services in cooperation with the data store and is able to generate content such as text, graphics, audio, and/or video to be transferred to the user, which may be served to the user by the Web server in the form of HyperText Markup Language ("HTML"), Extensible Markup Language ("XML"), or another appropriate structured language in this example. The handling of all requests and responses, as well as the delivery of content between the system 10 and the application server 1408, can be handled by the Web server. It should be understood that the Web and application servers are not required and are merely example components, as structured code discussed herein can be executed on any appropriate device or host machine as discussed elsewhere herein.

The data store 1410 can include several separate data tables, databases or other data storage mechanisms and media for storing data relating to a particular aspect. For example, the data store illustrated includes mechanisms for storing production data 1412 and user information 1416, which can be used to serve content for the production side. The data store also is shown to include a mechanism for storing log data 1414, which can be used for reporting, analysis, or other such purposes. It should be understood that there can be many other aspects that may need to be stored in the data store, such as for page image information and to access right information, which can be stored in any of the above listed mechanisms as appropriate or in additional mechanisms in the data store 1410. The data store 1410 is operable, through logic associated therewith, to receive instructions from the application server 1408 and obtain, update or otherwise process data in response thereto. In one example, a user might submit a search request for a certain type of item. In this case, the data store might access the user information to verify the identity of the user and can access the catalog detail information to obtain information about items of that type. The information then can be returned to the user, such as in a results listing on a Web page that the user is able to view via a browser on the electronic device 16. Information for a particular item of interest can be viewed in a dedicated page or window of the browser.

Each server typically will include an operating system that provides executable program instructions for the general administration and operation of that server and typically will include a computer-readable storage medium (e.g., a hard disk, random access memory, read only memory, etc.) storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 15. Thus, the depiction of the system 1400 in FIG. 15 should be taken as being illustrative in nature and not limiting to the scope of the disclosure.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as Transmission Control Protocol/Internet Protocol ("TCP/IP"), Open System Interconnection ("OSI"), File Transfer Protocol ("FTP"), Universal Plug and Play ("UpnP"), Network File System ("NFS"), Common Internet File System ("CIFS"), and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including Hypertext Transfer Protocol ("HTTP") servers, FTP servers, Common Gateway Interface ("CGP") servers, data servers, Java servers, and business application servers. The server(s) also may be capable of executing programs or scripts in response to requests from user devices, such as by executing one or more Web applications that may be implemented as one or more scripts or programs written in any programming language, such as Java®, C, C#, or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit ("CPU"), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired)), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory ("EEPROM"), flash memory or other memory technology, Compact Disc Read-Only Memory ("CD-ROM"), digital versatile disk (DVD), or other optical storage, magnetic cassettes, magnetic tape, magnetic disk storage, or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for detecting whether a target virus is present in a biological sample, the system comprising:
a cartridge comprising an outer shell, a swab tube slidably mounted within the outer shell, a lysis buffer container storing a lysis buffer, a virus detection assembly (VDA), and a control detection assembly (CDA); wherein the VDA comprises a VDA vacuum port, a VDA vacuum chamber fluidly connected to the VDA vacuum port, a VDA fluid displacement port, a VDA hydration water chamber storing hydration water and fluidly connected to the VDA fluid displacement port, a VDA lysis transfer tube fluidly connected to the swab tube, a VDA lysis well fluidly connected to the VDA lysis transfer tube, the VDA vacuum chamber, and the VDA hydration water chamber, a VDA amplification cycle well fluidly connected to the VDA lysis well and containing a VDA amplification cycle bead, a VDA detection cycle well fluidly connected to the VDA amplification cycle well and containing a VDA detection cycle bead, and a VDA fluorescence reading chamber fluidly connected to the VDA amplification cycle well; wherein the CDA comprises a CDA vacuum port, a CDA vacuum chamber fluidly connected to the CDA vacuum port, a CDA fluid displacement port, a CDA hydration water chamber storing hydration water and fluidly connected to the CDA fluid displacement port, a CDA lysis transfer tube fluidly connected to the swab tube, a CDA vacuum port, a CDA fluid displacement port, a CDA hydration water chamber storing hydration water, a CDA lysis transfer tube, a CDA lysis well fluidly connected to the CDA lysis transfer tube, the CDA vacuum chamber, and the CDA hydration water chamber, a CDA amplification cycle well fluidly connected to the CDA lysis well and containing a CDA amplification cycle bead, a CDA detection cycle well containing a CDA detection cycle bead, and a CDA fluorescence reading chamber fluidly connected to the CDA amplification cycle well; wherein the swab tube is configured to receive a portion of a swab on which a biological sample is disposed; and wherein the swab tube comprises a swab tube distal end configured to create an opening in the lysis buffer container during a user-induced distal sliding of the swab tube relative to the outer shell to create an opening in the lysis buffer container to release the cartridge is reconfigurable to a portion of the lysis buffer to contact the swab to form a sample infused lysis buffer solution;
an analysis device comprising a housing, a cartridge support assembly, a controller, a VDA vacuum pump, a VDA vacuum pump nozzle fluidly connected to the VDA vacuum pump, a VDA positive displacement pump, a VDA positive displacement pump nozzle fluidly connected to the VDA positive displacement pump, a CDA vacuum pump, a CDA vacuum pump nozzle fluidly connected to the CDA vacuum pump, a CDA positive displacement pump, a CDA positive displacement pump nozzle fluidly connected to the CDA positive displacement pump, a VDA lysis well heating element, a VDA reaction well heating element, a VDA detection well heating element, a CDA lysis well heating element, a CDA reaction well heating element, a CDA detection well heating element, a VDA light emitter, a VDA fluorescence light detector, a CDA light emitter, a CDA fluorescence light detector, a cartridge support configured to receive and accommodate the cartridge, wherein the cartridge support assembly is operable to operably couple the VDA vacuum pump nozzle to the VDA vacuum port, the VDA positive displacement pump nozzle to the VDA fluid displacement port, the CDA vacuum pump nozzle to the CDA vacuum port, the CDA positive displacement pump nozzle to the CDA fluid displacement port; and wherein the controller is configured to:

operate the VDA vacuum pump to draw a portion of the sample infused lysis buffer solution through the VDA lysis transfer tube from the swab tube to the VDA lysis well, operate the CDA vacuum pump to draw a portion of the sample infused lysis buffer solution through the CDA lysis transfer tube from the swab tube to the CDA lysis well, operate the VDA lysis well heating element to heat the sample infused lysis buffer solution in the VDA lysis well to within a VDA lysis temperature range for a VDA lysis period of time to form a VDA post-lysis sample solution;

operate the CDA lysis well heating element to heat the sample infused lysis buffer solution in the CDA lysis well to within a CDA lysis temperature range for a CDA lysis period of time to form a CDA post-lysis solution;

operate the VDA positive displacement pump to transfer the VDA post-lysis sample solution from the VDA lysis well and hydration water from the VDA hydration water chamber to the VDA amplification cycle well to rehydrate the VDA amplification cycle bead and form a VDA amplification cycle liquid in the VDA amplification cycle well;

operate the CDA positive displacement pump to transfer the CDA post-lysis solution from the CDA lysis well and hydration water from the CDA hydration water chamber to the CDA amplification cycle well to rehydrate the CDA amplification cycle bead and form a CDA amplification cycle liquid in the CDA amplification cycle well;

operate the VDA amplification well heating element to heat the VDA amplification cycle liquid in the VDA amplification cycle well to within a VDA amplification cycle temperature range for a VDA amplification cycle period of time to form a VDA amplified sample solution;

operate the CDA amplification well heating element to heat the CDA amplification cycle liquid in the CDA amplification cycle well to within a CDA amplification cycle temperature range for a CDA amplification cycle period of time to form a CDA amplified sample solution;

operate the VDA positive displacement pump to transfer the VDA amplified sample solution from the VDA amplification cycle well to the VDA detection cycle well to rehydrate the VDA detection cycle bead to form a VDA detection cycle liquid in the VDA detection cycle well;

operate the CDA positive displacement pump to transfer the CDA amplified sample solution from the CDA amplification cycle well to the CDA detection cycle well to rehydrate the CDA detection cycle bead to form a CDA detection cycle liquid in the CDA detection cycle well;

operate the VDA detection well heating element to maintain the VDA detection cycle liquid in the VDA detection cycle well within a VDA detection cycle temperature range for a VDA detection cycle period of time;

operate the CDA detection well heating element to maintain the CDA detection cycle liquid in the CDA detection cycle well within a CDA detection cycle temperature range for a CDA detection cycle period of time;

operate the VDA positive displacement pump to transfer the VDA detection cycle liquid from the VDA detection cycle well to the VDA fluorescence reading chamber;

operate the CDA positive displacement pump to transfer the CDA detection cycle liquid from the CDA detection cycle well to the CDA fluorescence reading chamber;

operate the VDA light emitter to emit a VDA fluorescence excitation light onto the VDA detection cycle liquid in the VDA fluorescence reading chamber so that the VDA fluorescence light detector generates a VDA fluorescence light emission detection signal in response to a VDA fluorescence light emitted by the VDA detection cycle liquid in the VDA fluorescence reading chamber;

operate the CDA light emitter to emit a CDA fluorescence excitation light onto the CDA detection cycle liquid in the CDA fluorescence reading chamber so that the CDA fluorescence light detector generates a CDA fluorescence light emission detection signal in response to a CDA fluorescence light emitted by the CDA detection cycle liquid in the CDA fluorescence reading chamber;

generate, based on the VDA fluorescence light emission detection signal and the CDA fluorescence light emission detection signal, detection data indicative of whether the target virus is present in the biological sample and/or whether the biological sample is sufficient for detecting whether the target virus is present in a biological sample; and transmit the detection data to an electronic device via a communication connection for processing and/or communication to a user.

2. The system of claim 1, wherein:

the VDA comprises a VDA lysis module and a VDA detection module, the VDA lysis module comprises the VDA lysis well, the VDA detection module comprises the VDA amplification cycle well, the VDA detection cycle well, and the VDA fluorescence reading chamber, the VDA detection module is slidably mounted within the housing and is displaced relative to the housing via displacement the user-induced distal sliding of the swab tube relative to the housing so as to place the VDA detection module in fluid communication with the VDA lysis module, the CDA comprises a CDA lysis module and a CDA detection module, the CDA lysis module comprises the CDA lysis well, the CDA detection module comprises the CDA amplification cycle well, the CDA detection cycle well, and the CDA fluorescence reading chamber, and the CDA detection module is slidably mounted within the housing and is displaced relative to the housing via the user-induced distal sliding of the swab tube relative to the housing so as to place the CDA detection module in fluid communication with the CDA lysis module.

3. The system of claim 1, wherein:
the cartridge support assembly comprises a cartridge input mechanism operable to reposition the cartridge support relative to the housing to reconfigure the analysis device between an open configuration and a closed configuration;
the open configuration accommodates interfacing the cartridge with the cartridge support and removal of the cartridge from the cartridge support;
reconfiguration of the analysis device from the open configuration to the closed configuration operatively couples the VDA vacuum pump nozzle to the VDA vacuum port, the VDA positive displacement pump nozzle to the VDA fluid displacement port, the CDA vacuum pump nozzle to the CDA vacuum port, and the CDA positive displacement pump nozzle to the CDA fluid displacement port;
the analysis device comprises a cooling fan configured to cool the cartridge, and
the controller blocks operation of the cartridge input mechanism to block reconfiguration of the analysis device from the closed configuration to the open configuration while a temperature of the cartridge is above an acceptable ejection temperature for the cartridge.

4. The system of claim 3, wherein the detection data comprises a detection result indicating whether the target virus is present in the biological sample and/or whether the biological sample is sufficient for detecting whether the target virus is present in a biological sample.

5. The system of claim 1, configured for detecting whether two or more viruses are present in a biological sample, wherein:
the two or more viruses comprise the target virus; and
the two or more viruses comprise at least one of SARS-CoV-2, Adenovirus, Coronavirus HKU1, Coronavirus NL63, Coronavirus 229E, Coronavirus OC43, Human Metapneumovirus, Human Rhinovirus, Human Enterovirus, Influenza A, Influenza A/H1, Influenza A/H1-2009, Influenza A/H3, Influenza B, Parainfluenza 1, Parainfluenza 2, Parainfluenza 3, Parainfluenza 4, Respiratory Syncytial Virus, Adenovirus F40/41, Astrovirus, Norovirus GI, Norovirus GII, Rotavirus A, Sapovirus I, Sapovirus II, Sapovirus IV, and Sapovirus V.

6. A detection system for detecting a target virus, the detection system comprising:
a cartridge comprising an outer shell, a lysis buffer container storing a lysis buffer a swab tube, a vacuum port, a vacuum chamber fluidly connected to the vacuum port, a fluid displacement port, a hydration water chamber storing hydration water and fluidly connected to the fluid displacement port, a lysis transfer tube fluidly connected to the swab tube, a lysis well fluidly connected to the lysis transfer tube, an amplification cycle well fluidly connected to the lysis well and containing an amplification cycle bead, a detection cycle well fluidly connected to the amplification cycle well and containing a detection cycle bead, and a fluorescence reading chamber fluidly connected to the detection cycle well; wherein the swab tube is configured to receive a portion of a swab on which a biological sample is disposed; and wherein the cartridge is reconfigurable to cause a portion of the lysis buffer to contact the swab to form a sample infused lysis buffer solution;
an analysis device comprising a housing, a cartridge support assembly, a vacuum pump, a vacuum pump nozzle fluidly connected to the vacuum pump, a positive displacement pump, a positive displacement pump nozzle fluidly connected to the positive displacement pump, a light emitter, a fluorescence light detector, and a controller; wherein the cartridge support assembly comprises a cartridge support configured to receive and accommodate the cartridge, wherein the cartridge support assembly is operable to operably couple the vacuum pump nozzle to the vacuum port and the positive displacement pump nozzle to the fluid displacement port, and wherein the controller is configured to:
operate the vacuum pump to draw a portion of the sample infused lysis buffer solution through the lysis transfer tube from the swab tube to the lysis well,
operate the lysis well heating element to heat the sample infused lysis buffer solution in the lysis well to within a first temperature range for a first period of time to form a post-lysis sample solution,
operate the positive displacement pump to transfer at least a portion of the post-lysis sample solution from the lysis well and hydration water from the hydration water chamber to the amplification cycle well to rehydrate the amplification cycle bead to form an amplified sample solution in the amplification cycle well,
operate the positive displacement pump to transfer at least a portion of the amplified sample solution from the amplification cycle well to the detection cycle well to rehydrate the detection cycle bead to form a detection cycle liquid in the detection cycle well,
operate the positive displacement pump to transfer at least a portion of the detection cycle liquid from the detection cycle well to the fluorescence reading chamber,
operate the light emitter to emit a fluorescence excitation light onto the detection cycle liquid in the fluorescence reading chamber so that the fluorescence light detector generates a fluorescence light emission detection signal in response to a fluorescence light emitted by the detection cycle liquid,
generate, based on the fluorescence light emission detection signal, detection data indicative of whether the target virus is detected in the biological sample; and
transmit the detection data to an electronic device via a communication connection.

7. The detection system of claim 6, wherein:
the swab tube is slidably mounted within the outer shell to accommodate an induced displacement of the swab tube relative to the outer shell,
the cartridge comprises a lysis module and a detection module,
the lysis module comprises the lysis well,
the detection module comprises the amplification cycle well, the detection cycle well, and the fluorescence reading chamber,
the detection module is slidably mounted within the outer shell and is displaced relative to the outer shell via the induced displacement of the swab tube relative to the outer shell so as to place the detection module in fluid communication with the lysis module, and the induced displacement of the swab tube relative to the outer shell ruptures a membrane that isolated the lysis buffer from the swab.

8. The detection system of claim 7, wherein the detection module is hermetically sealed prior to being placed in fluid communication with the lysis module via the induced displacement of the swab tube relative to the outer shell.

9. The detection system of claim 6, wherein:
the cartridge support assembly comprises a cartridge input mechanism operable to reposition the cartridge support relative to the outer shell to reconfigure the analysis device between an open configuration and a closed configuration,
the open configuration accommodates interfacing the cartridge with the cartridge support and removal of the cartridge from the cartridge support,
reconfiguration of the analysis device from the open configuration to the closed configuration operatively couples the vacuum pump nozzle to the vacuum port and the positive displacement pump nozzle to the fluid displacement port.

10. The detection system of claim 9, wherein:
the analysis device comprises a cooling fan configured to cool the cartridge, and
the controller blocks operation of the cartridge input mechanism to block reconfiguration of the analysis device from the closed configuration to the open configuration while a temperature of the cartridge is above an acceptable ejection temperature for the cartridge.

11. The detection system of claim 9, wherein:
the cartridge input mechanism comprises a stepper motor; and
the controller monitors electric power supplied to the stepper motor and cuts off supply of electric power to the stepper motor in response to a magnitude of the electric power exceeding a power limit.

12. The detection system of claim 6, wherein the analysis device comprises an ultrasound generator that emits ultrasound to agitate the swab and the lysis buffer contacted with the swab.

13. The detection system of claim 6, wherein the analysis device comprises an optical filter configured to limit the fluorescence light emitted by the detection cycle liquid that is detected by the fluorescence light detector to wavelengths between 500 and 550 nm.

14. The detection system of claim 13, wherein the analysis device comprises a blue filter to limit wavelengths of the fluorescence excitation light that reaches the detection cycle liquid.

* * * * *